United States Patent
Peszynski et al.

(10) Patent No.: US 6,663,578 B1
(45) Date of Patent: *Dec. 16, 2003

(54) OPERATOR SUPERVISED TEMPERATURE CONTROL SYSTEM AND METHOD FOR AN ULTRASOUND TRANSDUCER

(75) Inventors: Michael Peszynski, Newburyport, MA (US); David Miller, Woburn, MA (US); Ivan Salgo, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/269,144

(22) Filed: Oct. 11, 2002

(51) Int. Cl.$^7$ .................................................. A61H 1/00
(52) U.S. Cl. ........................................... 601/2; 600/437
(58) Field of Search ................................ 601/2, 1, 159, 601/169; 600/437, 438, 459, 462, 466, 467, 471, 439; 604/22; 607/102

(56) References Cited

U.S. PATENT DOCUMENTS

| | | | |
|---|---|---|---|
| 4,638,436 A | * | 1/1987 | Badger et al. .............. 607/102 |
| 5,213,103 A | | 5/1993 | Martin et al. |
| 5,555,887 A | | 9/1996 | Fraser et al. |
| 5,560,362 A | | 10/1996 | Sliwa, Jr. et al. |
| 5,721,463 A | | 2/1998 | Snyder |
| 6,001,069 A | * | 12/1999 | Tachibana et al. .............. 601/2 |
| 6,210,356 B1 | | 4/2001 | Anderson et al. |

* cited by examiner

Primary Examiner—Dennis Ruhl
Assistant Examiner—Ruby Jain
(74) Attorney, Agent, or Firm—John Vodopia (57) ABSTRACT

A system and method for controlling the heat of an ultrasonic transducer is disclosed. In the presently preferred embodiments, the operator selects one or more mutable system parameters of the ultrasound system which will be changed if either the temperature becomes too great, or at the operator's command, or both.

18 Claims, 6 Drawing Sheets

OPERATOR SUPERVISED TEMPERATURE CONTROL SYSTEM AND METHOD FOR AN ULTRASOUND TRANSDUCER

BACKGROUND OF THE INVENTION

1. Field of the Invention

The invention relates generally to the field of imaging ultrasonic medical transducer assemblies, and, specifically, to an apparatus and method for cooling the transducer.

2. Description of the Related Art

Ultrasonic medical transducers are used to observe the internal organs of a patient. The ultrasonic range is described essentially by its lower limit: 20 kHz, roughly the highest frequency a human can hear. The medical transducers emit ultrasonic pulses which echo (i.e., reflect), refract, or are absorbed by structures in the body. The reflected echoes are received by the transducer and these received signals are translated into images. Such translation is possible because the reflections from the internal organs vary in intensity according to the "acoustic impedance" between adjacent structures. The acoustic impedance of a tissue is related to its density; the greater the difference in acoustic impedance between two adjacent tissues the more reflective their boundary will be.

The frequency of the ultrasonic beams has an effect on both the image resolution and the penetration ability of the ultrasonic device. Higher frequency ultrasound waves have a longer near field (i.e., the region in the sound beam's path where the beam diameter decreases as the distance from the transducer increases) and less divergence in the far field (i.e., the region in the sound beam's path where the beam diameter increases as the distance from the transducer increases): higher frequency ultrasonic waves thus permit greater resolution of small structures. However, high frequency ultrasonic waves have less penetrating ability because their energy is absorbed and scattered by soft tissues. On the other hand, lower frequency ultrasonic waves have a greater depth of penetration, but the received images are much less well defined. The conventional frequency range for imaging human internal organs (using sound waves) is typically from about 3 MHz to about 5 MHz.

Two types of resolution generally apply to ultrasound imaging transducers: lateral resolution and axial resolution. Lateral resolution is the ability to resolve objects side by side and, as discussed above, is proportionally affected by the frequency (the higher the frequency, the higher the lateral resolution). Higher frequency transducers are used for infants and children because there is less need for deep penetration and the smaller structures can be viewed with greater lateral resolution. Lower frequencies are used for adults where the internal structures are larger and there is a greater need for depth penetration. Of course, when determining the appropriate frequency to be used, the structure, tissue, or organ to be viewed (and the exact purpose of the imaging) can matter more than the age of the subject. For example, diagnostic breast imaging on an adult may require a frequency of about 7 MHz or higher.

Axial resolution is the ability to resolve objects that lie one above the other. Because this is related to depth penetration, axial resolution is inversely proportional to the frequency of the transducer (depending on the size of the patient). In large patients, higher frequency beams are rapidly absorbed by the objects closest to the transducer, thus reducing depth penetration and axial resolution.

The focusing of an ultrasonic transducer can be implemented in one of two ways: mechanical or electronic. Mechanical focusing consists of placing an acoustic lens on the surface of the transducer or using a transducer with a concave face. One or several piezoelectric elements are used. In order to create a sweeping beam for 2D imaging, a single element may be oscillated back and forth, several elements may be rotated, or a single element may be used with a set of acoustic mirrors. This last transducer type (with the acoustic mirrors) is sometimes called the "wobbler" because of the vibration created as the mirrors rotate or oscillate inside the housing.

Figure 1:
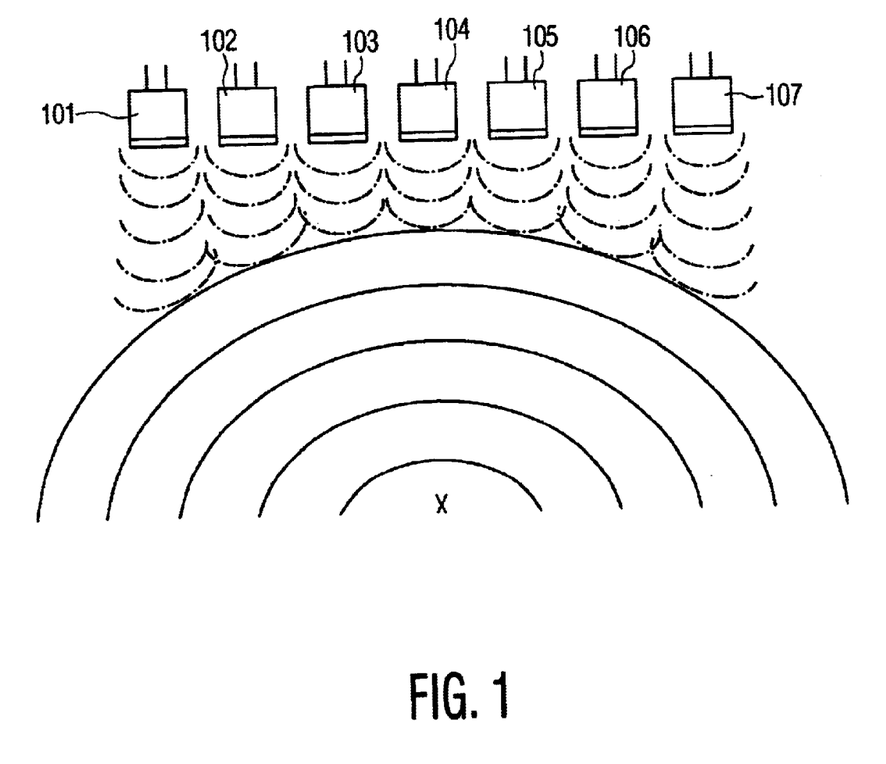
FIG. 1 shows how typical ultrasonic beam is formed by a linear array of piezoelectric elements.

Electronic focusing uses a process called phased array, where multiple piezoelectric elements in an array are stimulated (or "fired") sequentially in order to form and focus the beam. In an annular array, circular or ringlike elements and/or arrays are used. In a linear array, a row of elements is used to form and focus the beam. A transducer contains an array of transmitting elements and a similar array of receiving elements. An example of how a linear array form is and focuses a sound beam is shown in FIG. 1. In order to focus at point X, the outer elements 101 and 107 fire first, then elements 102 and 106, then elements 103 and 105, and finally element 104. As shown in FIG. 1, the resulting wavefronts combine to form a semicircular ultrasonic pulse whose focal point is X. By varying the sequential pattern of firing, the distance of focal point X from the transducer can be changed. Furthermore, varying the sequential pattern of firing can also be used to steer the beam. Steering is used to move focal point X left and right in FIG. 1. By rapidly steering a series of beams from left to right, a 2D cross-sectional image may be formed.

In 2D mode, one sweep from left to right is a frame, and the number of sweeps in a second is the frame rate (or fps—frames per second). Conventional frame rates ranges from about 12 fps to about 30 fps. The number of beams formed over time is the Pulse Repetition Frequency (PRF), measured in pulses per second. The range of PRFs for most commercial echocardiographs is between about 200 and about 5000 pulses per second. PRF varies with the type of imaging being performed. Most of the time spent in each second is used waiting for the echoes to return to the receiving elements in the transducer. In other word s, after a beam is formed, the transmitting elements lie dormant while the beam travels to the various objects and then some of that sound energy returns (as echoes) to the transducer's receiving elements. The amount of time that the transmitting elements are transmitting sound energy is called the duty factor. Most transducers are acting as a receiver about 99% of the time, in which case the duty factor is 1(%).

Aperture is the size of the active transmitting and receiving portion of a transducer array. Aperture is measured in square centimeters and is a function of the number of transducer elements used simultaneously to form an image. A common measurement of aperture size is F-number or F#, which is defined as the ratio of depth to aperture. These values are related to the lateral resolution (LR) by the following function:

$$LR = \lambda * F\# = \lambda * \frac{D}{A}$$

where=wavelength of sound pulse
D=depth of the scan
A=aperture of the scan

As can be seen from the above equation, for a fixed frequency, the aperture size must increase as the scanning depth increases in order to maintain uniform lateral resolution throughout the image. Many ultrasonic systems select a transmit aperture based on the scan depth setting and continuously vary the reception aperture. It is desirable to achieve low F#s, which, because the scanning depth is limited by the position of the desired subject, is identical to seeking larger aperture sizes. It is also desirable to seek small wavelengths, which is equivalent to seeking higher frequencies.

There are a number of modes in which an ultrasonic transducer operates. The basic modes are A Mode, B Mode, M Mode, and 2D Mode. The A Mode is amplitude mode, where signals are displayed as spikes that are dependent on the amplitude of the returning sound energy. The B Mode is brightness mode, where the signals are displayed as various points whose brightness depends on the amplitude of the returning sound energy. The M Mode is motion mode, where B Mode is applied and a strip chart recorder allows visualization of the structures as a function of depth and time. The 2D Mode is two-dimensional (imaging) mode, where B Mode is spatially applied by sweeping the beam (as described above) so that structures are seen as a function of depth and width.

2D Mode refers to the most basic, fundamental imaging mode. There are other imaging modes, which also image in two dimensions (in three dimensions in some new technologies), but these are referred to by their own names, usually based on the type of technology/methodology used to produce the image. Some of these other imaging modes will be described below. When the term 2D Mode is used, it only refers to the basic spatially oriented B Mode, and not all two dimensional imaging modes.

There have been various solutions to the problem of higher frequency-greater resolution-less depth penetration and lower frequency-lower resolution-greater depth penetration. One solution is harmonic imaging. With conventional imaging, the ultrasound system transmits and receives a sound pulse of a specific frequency (the "fundamental" frequency). As discussed above parts of the sound pulse are reflected back to the transducer, where the reflected sound at the fundamental frequency is processed. In harmonic imaging, the transducer does not listen for the fundamental frequency, but for other frequencies—most notably, the "harmonic" frequency, which is twice the fundamental frequency (this is sometimes referred to as the "first harmonic"). To be more technically accurate, the transducer receives a signal comprised of a number of frequencies, including the fundamental and harmonic, and separates out the signal at the harmonic frequency (the "harmonic" for short). Once separated out, the harmonic is processed to produce an image.

Harmonics are generated by the object being imaged, either with or without the assistance of human intervention. When assisted, harmonics are generated by ultrasound "contrast agents" which are injected into the patient's body. These contrast agents generally contain very small bubbles which generate two kinds of echoes when struck by a pulse. First, the conventional echo is bounced back based on the fundamental frequency. But then the bubble vibrates (in response to the pulse), thereby generating a harmonic signal. Because these contrast agents are formed for the purpose of creating harmonic echoes (rather like a bell when struck by a clapper), very strong echoes are generated at the harmonic frequency, thereby producing excellent high contrast images.

When not relying on contrast agents, harmonic imaging uses the harmonics that are generated by the tissue of the body itself (having been "rung" by the ultrasonic pulse). Obviously, these harmonics do not generate as clear a picture as the harmonics from contrast agents. The ability to create harmonics in tissue varies depending on the tissue's location in the ultrasound beam's field of view. The most pronounced imaging effect is from harmonics located at and around the focal point of the ultrasonic beam (i.e., mid-field). No harmonics are generated by tissue in the near field, and the harmonics generated in the far field attenuate quickly after being produced.

Harmonic imaging has a number of advantages. The beam formed at the harmonic frequency is narrower and has lower side-lobes, thereby significantly improving grayscale contrast resolution. Furthermore, since the harmonics are generated inside the body, they only pass through the fat layer once, rather than twice.

Some other modes of imaging are dependent on the Doppler effect, the phenomena whereby the frequency of sound from an approaching object has a higher frequency and, conversely, sound from a receding object has a lower frequency. In ultrasonic systems, this effect is used to determine the velocity and direction of blood flow in a subject. Doppler techniques can also be used with ultrasonic transducers which operate in continuous wave mode (i.e., part of the transducer array transmits while another part simultaneously receives).

Pulsed wave Doppler effect techniques have proven to be very accurate in blood flow studies. However, if the velocity of the blood flow being measured exceeds the Nyquist Limit (half the PRF), the ultrasonic readings become inaccurate. Most Doppler techniques try to achieve a high a PRF as possible in order to avoid this effect. One type of imaging, Color Flow Imaging or CFI, uses this effect (called "aliasing") to detect flow disturbances, e.g., transitions from laminar to turbulent flow. In CFI, multiple sample volumes are detected and displayed utilizing color mapping for direction and velocity flow data. Common mapping formats are BART (Blue Away, Red Towards), RABT (Red Away, Blue Towards), or enhanced/variance flow maps where color saturations indicate turbulence/acceleration and color intensities indicate higher velocities. Some maps use a third color, green, to indicate accelerating velocities and turbulence.

It is desirable for the ultrasonic system to operate at the highest frequency (for the reasons discussed above) and at the maximum acoustic intensity. Maximizing the acoustic intensity increases imaging performance by increasing the depth penetration and maximizing the signal to noise ratio (SNR). However, higher frequencies and greater acoustic intensities cause the ultrasonic transducer to heat up, and there are regulatory limits (and practical limits) on the surface temperature of an ultrasonic probe when interacting with a subject. Specifically, the upper temperature limit on the patient contact surface of an ultrasonic transducer is generally considered to be about 41° C. or about 16° C. above ambient temperature.

The heat of the transducer surface is generated both by the electroacoustic energy conversion process taking place in the transducer's piezoelements and by the acoustic energy passing, through and/or into adjacent transducer materials (and the patient herself). Different methods and systems have been developed to deal with the heating problem and they can be broken into two types: active and passive. Passive solutions use passive cooling mechanisms, i.e., spreading out the dissipated heat to as large an external transducer surface area as possible. Typically, the heat generated by the transducer array is absorbed by solid thermal conductors, and then this captured heat is moved by thermal convection into the transducer's external case, where it can dissipate in the atmosphere. Ideally, the external heat-convecting surface area would consist of the transducer's entire external surface area.

Figure 2:
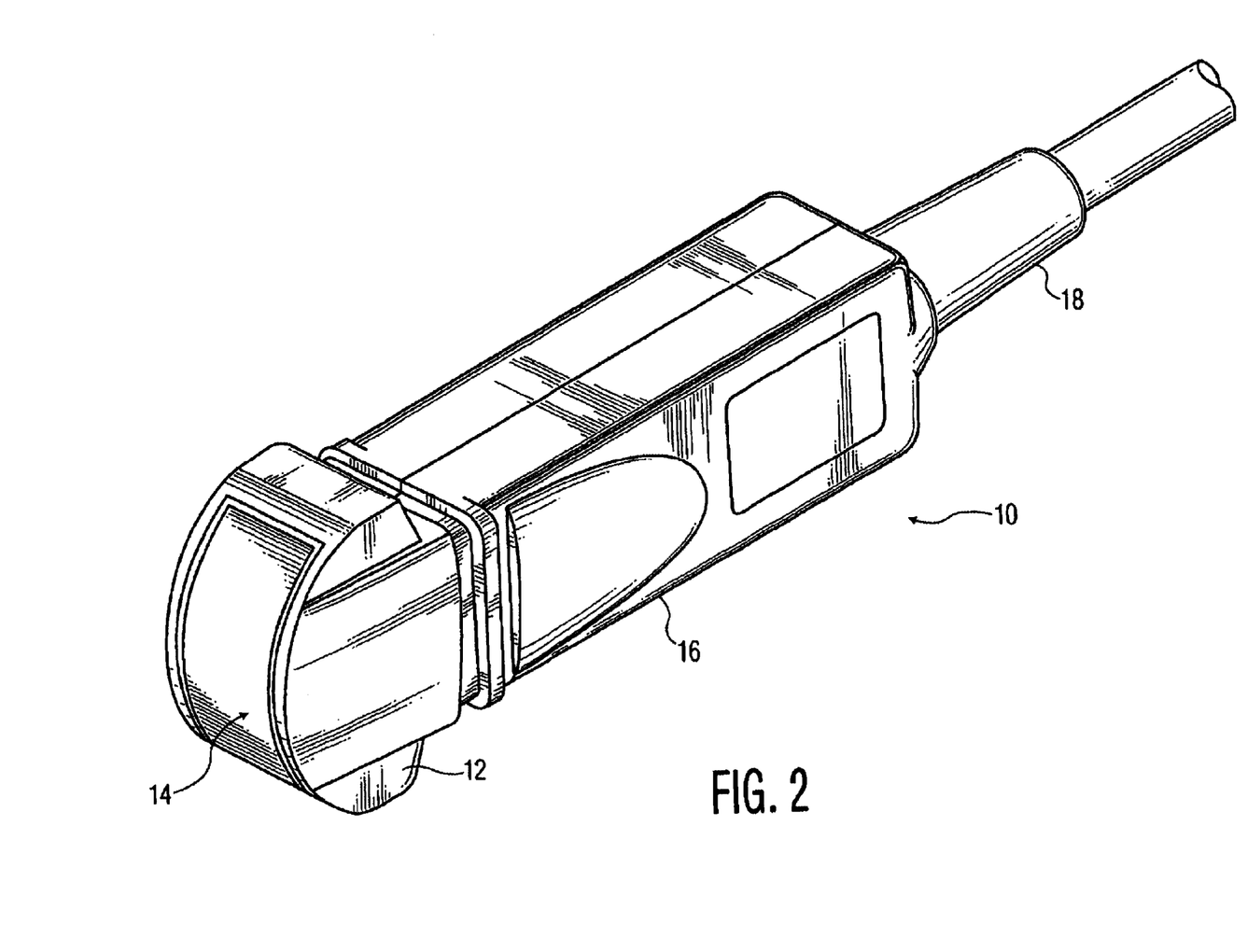
FIG. 2 shows a prior art ultrasonic transducer probe.

One example of a passive heat dissipation system is U.S. Pat. No. 5,213,103 ('103 patent), which is hereby incorporated by reference in its entirety. FIG. 2 shows the outside of the transducer in the '103 patent. A heat sink device (internal to the transducer, thus not shown) placed inside the transducer 10 behind the piezoelectric elements in the face 14 (i.e., the patient contact surface) on the head 12 of transducer 10. The heat sink extends the entire length of the transducer and conducts heat away from face 14, through head 12, to the sides of handle 16 and power cable 18. Heat conductive epoxy is used both to attach the heat sink to the transducer housing and to conduct the heat from the heat sink to the transducer housing.

Another example of a passive heat dissipation system is U.S. Pat. No. 5,555,887 ('887 patent), which is hereby incorporated by reference in its entirety. The '887 patent applies heat dissipation to an endoscopic ultrasound transducer by embedding aluminum foil in acoustic lens material in front of the transducer array. Heat is conducted by the aluminum foil to a heat sink positioned at a distance from the patient contacting surface of the probe. U.S. Pat. No. 5,721,463 ('463 patent), which is hereby incorporated by reference in its entirety, describes a passive heat dissipation system which uses a bundle of coaxial cables to vent heat away from the face of the probe.

These passive heat sinks are effective, but they also add to the transducer's overall thermal dissipation resistance. The fundamental limitation is that, for most transducers, even if heat is spread uniformly on the external case surfaces, it only takes a few watts of transducer driving power to cause the average transducer surface temperature to become unacceptable either with respect to the patient or the sonographer. In these cases, and particularly for small transducers having small surface areas, one may find that one is unable to operate at the allowable acoustic intensity limit because of excessive temperatures.

Active solutions, on the other hand, use active cooling means, such as circulating coolant systems. One example, U.S. Pat. No. 5,560,362 ('362 patent), which is hereby incorporated by reference in its entirety, describes a heat dissipation system in which a pumping or pressurization means actively circulates a gaseous or liquid coolant in a cable, part of which is nearby the transducer array. The system can be a single pass, multipass, or closed loop circulating system, and the coolant may pass through a heat exchanger, a heat pipe, a thermoelectric cooler, an evaporator/condenser system, and/or a phase change material.

An ultrasonic transducer cooling system which uses feedback control is shown in U.S. Pat. No. 6,210,356 ('356 patent), which is hereby incorporated by reference in its entirety. The '356 patent is directed to a catheter which provides ultrasonic energy (and perhaps medicine) as a therapeutic treatment to a site inside a patient's body. Thus, no imaging or sensing is being performed by the ultrasonic transducer in the '356 patent. Temperature sensors are positioned in the surface coating of the catheter next to the ultrasound transducer in order to provide a measure of the temperature on the exterior surface of the catheter. This measure is used as a feedback control signal for the power circuits of the ultrasonic transducer. After the user sets a predetermined temperature, the power circuits decrease or increase power in the same proportion as the measured temperature is above or below the predetermined temperature.

The device described in the '356 patent also includes safety control logic which detects when the temperature at a temperature sensor has exceeded a safety threshold. When this occurs, the power circuits stop providing power to the ultrasonic transducer. However, such a feedback control system can be inappropriate for ultrasonic imaging/measuring applications.

Although abruptly turning off the power during a therapeutic ultrasonic session may not be damaging, abruptly turning off the power during an imaging/measuring session can be potentially dangerous (e.g., a sudden blackout during a surgical procedure). Even when not dangerous, turning off the image makes the diagnosis and analysis of image data difficult. Thus, there is a need for a system and method for reducing the temperature of the ultrasonic transducer in general, and the patient contacting surface in specific, which does not merely turn the transducer off. Furthermore, there is a need for a system and method which may work either as a replacement for the conventional active or passive heat dissipation systems or as an adjunct to them.

SUMMARY OF THE INVENTION

One object of the present invention is to provide a system and method for reducing the temperature of an imaging ultrasonic transducer in general, and the patient contacting surface in specific, without merely turning the transducer off.

Another object of the present invention is to provide a system and method for reducing the temperature of an imaging ultrasonic transducer which may work either as a replacement for the conventional active or passive heat dissipation systems or as an adjunct to them.

Yet another object of the present invention is to provide a system and method by which an operator of an imaging ultrasonic transducer system may control the manner in which the ultrasonic transducer system changes parameters in order to cool the ultrasonic transducer.

These and other objects are achieved by the present invention which provides a system and method for an operator to control the temperature of a ultrasonic transducer by changing mutable system parameters. The operator selects one or more mutable system parameters of the ultrasound system which will be changed if either the temperature becomes too great, or at the operator's command, or both.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

The present invention is directed to a novel system and method of controlling the radiant heat from the patient contact surface of an ultrasonic transducer. Although the details of implementation may be different in different embodiments, the present invention is not limited to any particular type of ultrasonic transducer, whether used internally or externally, or any particular mode of imaging and/or data analysis. The presently preferred embodiments of the present invention allow the operator to control the temperature of the transducer face by changing operating system parameters. In different embodiments, any one (or more) of the following may be under the control of the operator: which mutable system parameters are changed, when the selected mutable system parameters are changed, and how the mutable system parameters are changed.

In one preferred embodiment, the operator selects the mutable system parameters (and the type and amount of change) before the ultrasonic session begins; in another, the operator selects the mutable system parameters (and the type and amount of change) during the ultrasonic session.

Figure 3:
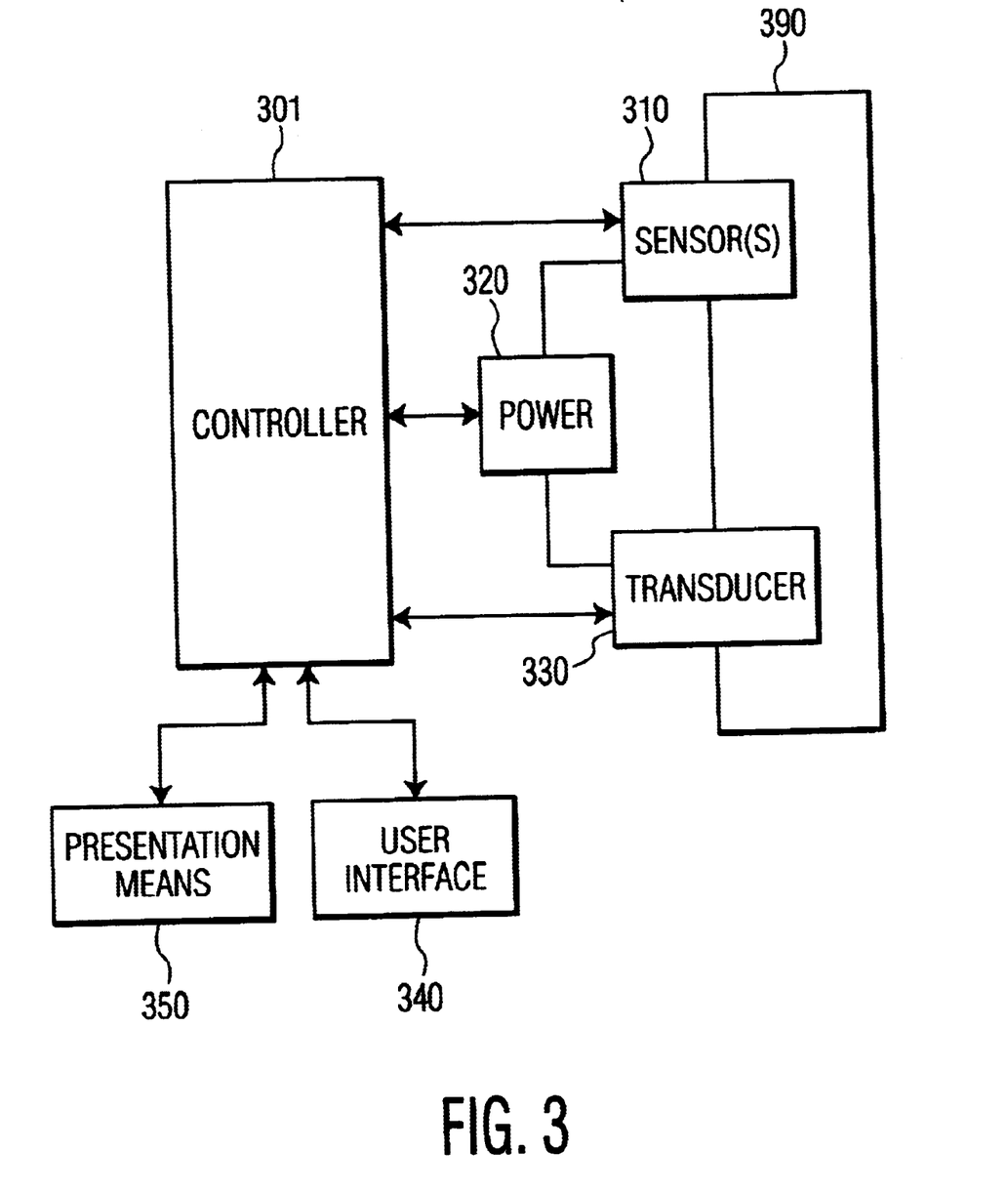
FIG. 3 is a block diagram showing the functional modules of an ultrasonic transducer system according to a preferred embodiment of the present invention.

A block diagram of the functional modules in a preferred embodiment of the present invention is shown in FIG. 3. Each of the functional modules should be understood as an abstraction of the function or combination of functions named, and each can be combined or further divided as necessary for implementing a particular embodiment. These functions may be implemented in software, hardware, or a combination of the two.

In FIG. 3, a controller 301, which may take the form of a microprocessor, controls the overall functioning of the ultrasonic device. Controller 301 receives measurement signals from temperature sensor(s) 310. Possible temperature sensors include any known conventional temperature sensor, such as, for example, thermistors, thermocouples, resistance temperature detectors (RTDs), and fiber optic temperature sensors which use thermalchromic liquid crystals. There may be one or more temperature sensor(s) 310, and their appropriate placement within the ultrasonic system will depend on the use and type of system, as would be known to one skilled in the art. In the preferred embodiments, the appropriate placement of the temperature sensor(s) 310 is the most suitable location to ascertain the surface temperature of the patient contacting surface 390 of the ultrasonic transducer.

Power supply 320, under control of controller 301, supplies power to the various components of the ultrasonic system. For example, controller 320 controls the amount of power sent to the ultrasonic transducer 330. Ultrasonic transducer 330 is also under the control of controller 301. The present invention is not limited to any particular type of imaging ultrasonic system, nor to any particular imaging or non-imaging mode. User interface 340 allows the user to monitor the condition of, and/or to interact with, the ultrasonic system; it may comprise a keyboard (and mouse), a microphone (and voice recognition software), a handheld input device, or any other form of input device compatible with the present invention. Presentation means 350 is for presenting system parameters, and may or may not be used to see the results of the ultrasonic testing being performed. Presentation means 350 may comprise a display monitor, a speaker (with either voice synthesis or pre-recorded speech), or any other means of presenting the status of system parameters and/or allowing the user to interact with the ultrasonic system.

Although not necessary, an ultrasonic system according to the present invention may also comprise a passive or active heat dissipation system. In some embodiments of the present invention, the present invention itself acts as the sole heat dissipation system for the ultrasonic transducer.

In an ultrasonic transducer system according to the present invention, the operator of the ultrasonic system can choose the system parameters which the system will alter (the "mutable system parameters") to avoid excessive temperatures at the patient contacting surface. In one preferred embodiment, the operator selects the mutable system parameters at the initial stage of the session, before starting the session with the patient. In another preferred embodiment, the ultrasonic system warns the operator that the temperature is dangerously close to excessive during the session and prompts the operator to choose one or more mutable system parameters to change in order to reduce the temperature on the patient contacting surface.

The mutable system parameters which can be altered in order to decrease the ultrasonic transducer temperature include, but are not limited to:

Duty Cycle—the system will reduce the amount of time the transmitting piezoelectric elements are active during each transmit-receive cycle.

Applied Voltage—the system decreases the voltage applied to the transmitting elements, which will result in reduced intensity (and temperature).

(Imaging) Mode—the system switches from a higher power imaging mode to a lower power imaging mode, e.g., from harmonic imaging to 2D (fundamental) imaging, from 3D imaging to 2D or harmonic imaging, from 2D mode to M mode, etc.

Frequency—the system decreases the frequency of the ultrasonic sound waves.

Frame Rate—the system decreases the frame rate (number of sweeps per second).

Pulse Repetition Frequency (PRF)—the system decreases the number of beams formed per second.

Aperture—the system decreases the size of the aperture.

(Imaging) Depth—the system decreases the scanning depth.

Sector Width—the system decreases the width of the zone being scanned.

When a mutable system parameter is selected by the operator, the amount or type of parameter change is also selected by the operator. This may be done in three basic formats: the system can offer specific values to choose from, can allow the operator to enter specific values, or a combination of both. Furthermore, the manner in which the mutable system parameters change may be rule-based, e.g., the operator may desire that one or more system parameters remain constant while the selected mutable system parameters change (thus requiring the system to alter other, unselected, mutable system parameters). For example, it may be desirable for the F# to stay constant during the session. Thus, if the aperture was selected as the mutable system parameter, the system will also need to alter the depth in order to insure that the F# remains a constant value. Rules may also be much more complex. For instance, a rule may take the form of: <if system parameter X is in state A, change parameter Y by Q amount, but if parameter Z is in state B (as well as X being in A), change parameter W to setting V>. In the preferred embodiments, the system has the rule formats already programmed, e.g., the <if-then> rule format or the <keep this parameter constant by varying those other parameters> rule format is a choice the operator selects, and then the operator fills in the blanks.

As another example, it may be more desirable to keep a constant image of current color flow than to keep a very accurate image. In this case, a list of mutable system parameters may be entered by the operator, where the list is in order of decreasing preference. The first mutable system parameter on the list may be applied voltage, or transmit power, while the second mutable system parameter may be frame rate. The system may keep decreasing the transmit power until it reaches a certain limit, e.g., 50% normal transmit power. Then, the system moves on to the second item on the list, frame rate, and begins to decrease that.

In the preferred embodiments, once the selected mutable system parameter is altered (i.e., changed to 50% normal transmit power), it remains altered for the remainder of the session, regardless of whether the temperature decreases to a safe level. In other embodiments, after a mutable system parameter has been altered because of high temperature, the system will check to see if the temperature has lowered to an appropriate level. If the temperature is appropriately reduced, the system will gradually return the altered mutable system parameter to its original state. In yet other embodiments, the operator controls if and when the system resets. Each embodiment may use any or a combination of these reset methods.

Figure 4:
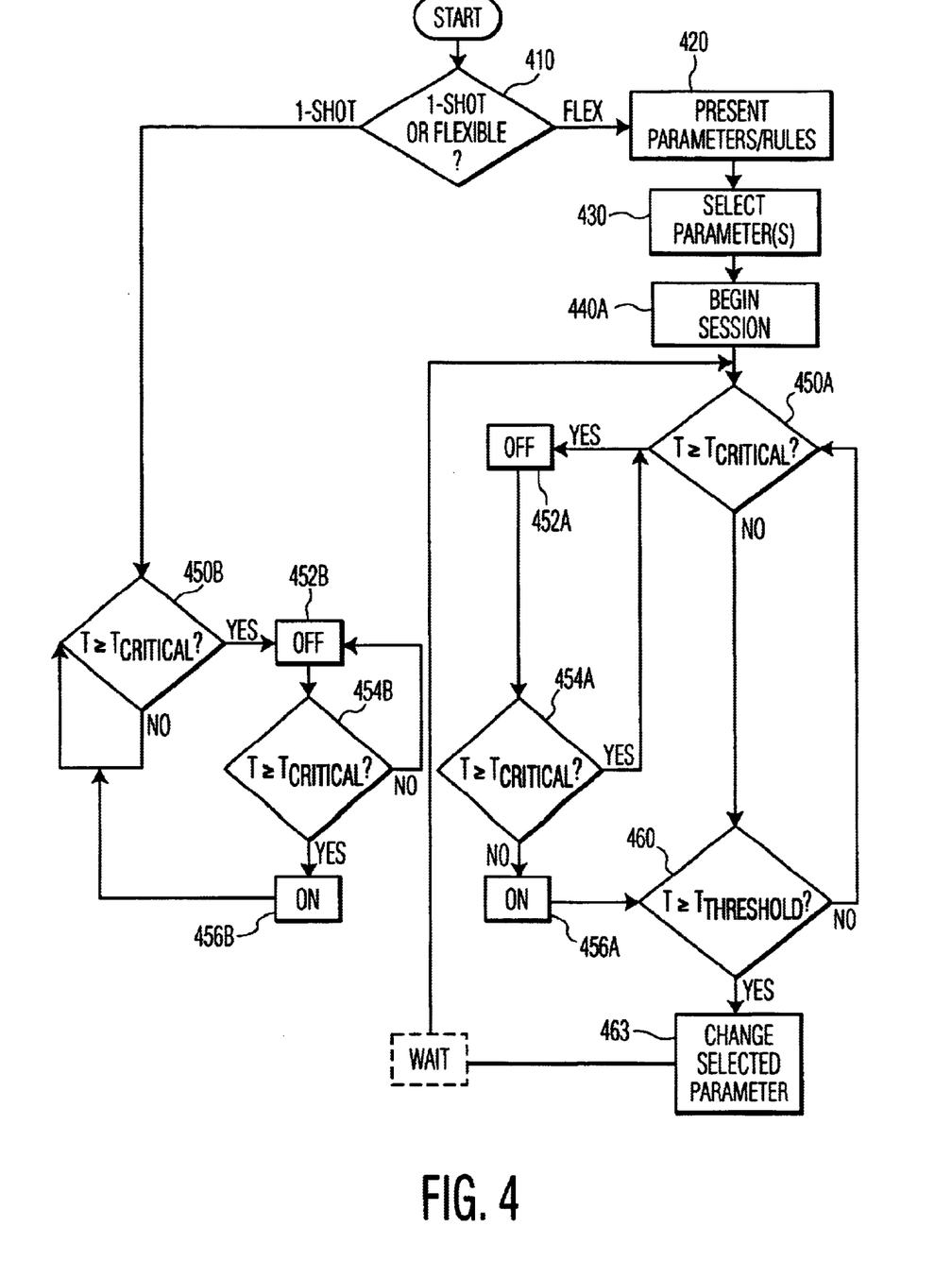
FIG. 4 is a flowchart of an overheating prevention method of one preferred embodiment according to the present invention.

One preferred embodiment, in which the operator chooses the mutable system parameters and/or the rule-based decision-making process of the ultrasonic system before the session begins, is shown in FIG. 4. After the ultrasonic system has started up, the operator must choose at step 410 which method to use for avoiding overheating: the one-shot strategy where the ultrasonic transducer simply turns off when a critical temperature $T_{critical}$ is reached, or the flexible strategy where mutable system parameters are changed when a threshold temperature $T_{threshold}$ is reached. In this context, the critical temperature $T_{critical}$ and the threshold temperature $T_{threshold}$ are different: at the critical temperature $T_{critical}$, the transducer must be turned off in order to avoid damaging the patient, whereas, at the threshold temperature $T_{threshold}$ (which is less than the critical temperature $T_{critical}$), one or more mutable system parameters must be reduced in order to avoid reaching the critical temperature $T_{critical}$.

If the operator chooses the flexible overheating prevention method, the ultrasonic system presents one or more menus of choices regarding mutable system parameters and/or possible rules concerning system parameters in step 420. In a preferred embodiment, this is structured as a series of menus and sub-menus which may be navigated by the operator using the ultrasonic systems' imaging display. The operator may use any appropriate tool for such on-screen navigation, including, but not limited to, an on-screen cursor controlled by a pointer such as a mouse. For example, the first menu page could ask <Which system parameter?> and have a list of all mutable system parameters for that system (or possibly the mutable system parameters for that particular session's use of the system).

The operator selects the parameter(s) in step 430. Depending on the embodiment, the selection step may include the system asking the operator whether he or she would like to enter a rule based on the selected parameter or simply enter a desired change in that parameter if the threshold temperature $T_{threshold}$ is reached. Furthermore, the system may present the option of creating a prioritized list of mutable system parameters. In some embodiments, the operator may also select the threshold temperature $T_{threshold}$ and/or the critical temperature $T_{critical}$.

In step 440, the ultrasonic session begins. If the operator had selected the one shot option in step 410, the process would have jumped to this step. In the following steps, the suffixes 'A' and 'B' are added to particular steps to indicate that the same action is being performed in each step, regardless of whether the system is in the flexible mode or the one-shot mode, respectively. Now that the session has begun, the system monitors the temperature sensors to determine if the temperature is greater than or equal to the critical temperature $T_{critical}$ in step 450A/450B. The use of feedback from temperature sensor is described in the U.S. patent application Ser. No. 10/268,261 entitled "Imaging Ultrasound Transducer Temperature Control System and Method using Feedback", filed on Oct. 10, 2002 and assigned to the same assignee as the present application. The aforementioned patent application is hereby incorporated by reference.

If the temperature is greater than or equal to the critical temperature $T_{critical}$ in step 450A/450B, the system turns off the ultrasonic transducer in step 452A/452B. The system keeps monitoring the temperature to see if it still equal to or above the critical temperature $T_{critical}$ in 454A/454B. If it is still too hot, the ultrasonic transducer remains off. If it is no longer too hot, the ultrasonic transducer is turned back on in step 456A/456B. In the one-shot mode, the system returns to monitoring the temperature in step 450B after turning the ultrasonic transducer in step 456B.

In the flexible mode in FIG. 4, after the ultrasonic transducer is turned back on in step 456A, or if the temperature is below the critical temperature $T_{critical}$ in step 450A, the system determines if the current temperature T is greater than or equal to the threshold temperature $T_{threshold}$ in step 460. If it is greater than or equal to the threshold temperature $T_{threshold}$, the system changes the selected mutable system parameter in step 463 in the manner chosen by the operator in step 430. This may take the form of a rule-based decision-making process as discussed above. Furthermore, if the system returns to step 463 a number of times within a certain period of time, the system may change the mutable system parameter by differing amounts as the mutable system parameter reaches a designated limit. For example, the operator may instruct the system to reduce the transmit power by an increasing percentage of the current total power (5%, 10%, 20%, etc.) until it reaches 50% of the total power when the session started. In another embodiment, step 460 determines whether the current temperature T is above or below a desired target temperature, where step 463 decreases or increases the mutable system parameter in order to reach the target temperature.

After the selected action has taken place in step 463, the system returns to monitoring the temperature in step 450A. A wait step may be added between step 463 and the return to step 450A in order that the selected action have an effect on the temperature before the system begins checking the temperature again. In the same vein, a timer may be added which will count down a predetermined period of time to allow for the temperature to start decreasing before readjusting the mutable system parameter again. If the current temperature T is not equal to or greater than the threshold temperature $T_{threshold}$ in step 460, the system returns to monitoring the temperature in step 450A. As mentioned above, in other embodiments, additional steps are added which allow the system to return the changed mutable system parameter to its original state, if the monitored temperature remains below the threshold temperature $T_{threshold}$ for a certain period of time.

Figure 5:
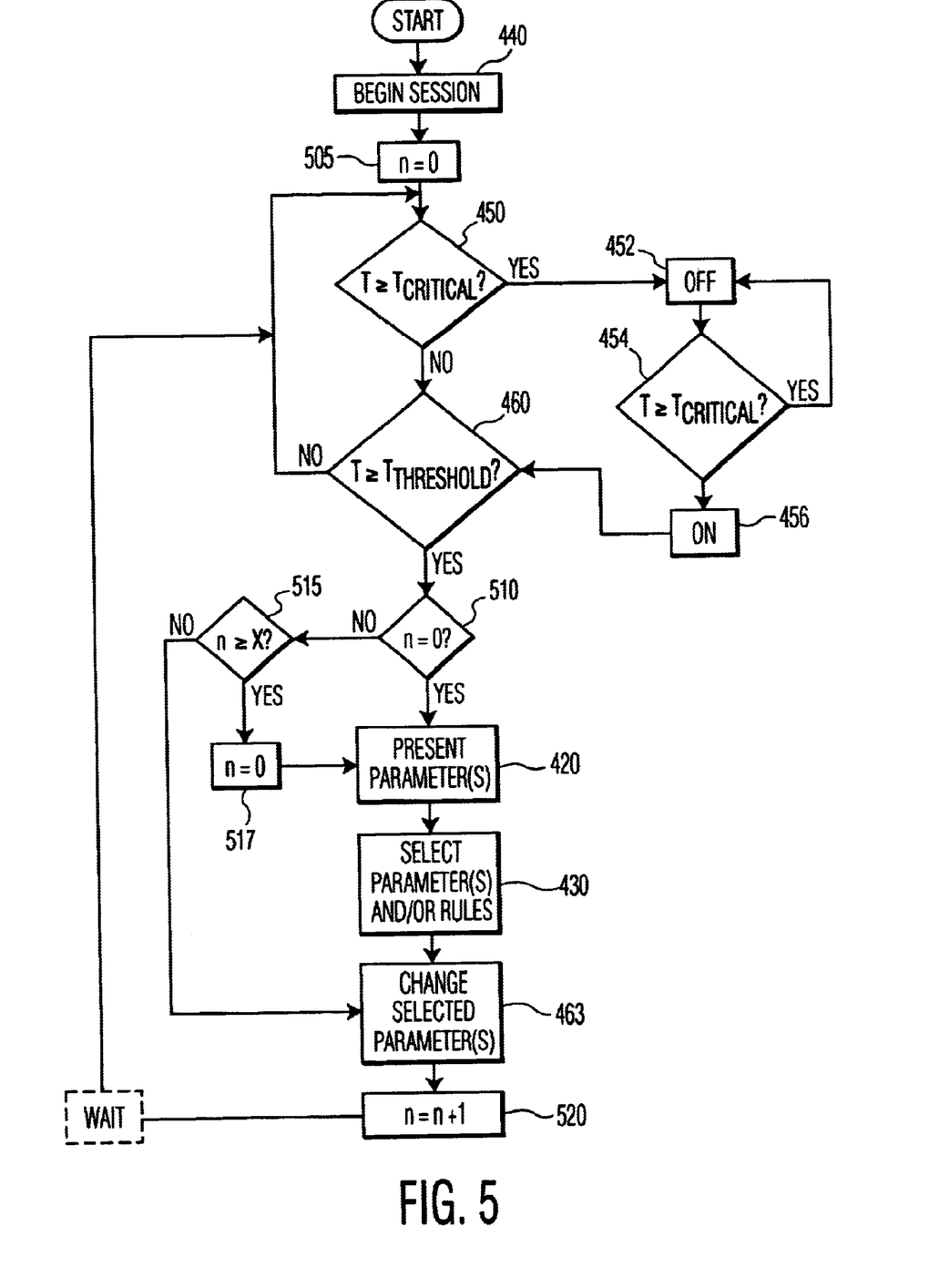
FIG. 5 is a flowchart of an overheating prevention method of another preferred embodiment according to the present invention.

Another preferred embodiment, in which the operator chooses the mutable system parameters and/or the rule-based decision-making process of the ultrasonic system during the session, is shown in FIG. 5. The same reference numbers are used for similar steps in FIG. 5 as in FIG. 4. In step 440, the ultrasonic session begins and the system sets a turn counter to 0 in step 505. The purpose of the turn counter is to count the number of times the presently chosen mutable parameter has been changed. If it has been changed too many times (the number x), the operator will be asked to choose another parameter. Obviously, x could be indefinite in some embodiments (thus eliminating steps 515 and 517), or 1 in other embodiments (thus eliminating steps 505, 510, 515, 517, and 520). At step 450, the system monitors the temperature sensors to determine if the temperature is greater than or equal to the critical temperature $T_{critical}$. If it is, the system turns off the ultrasonic transducer in step 452. The system keeps monitoring the temperature to see if it is still equal to or above the critical temperature $T_{critical}$ in 454. If it is still too hot, the ultrasonic transducer remains off. If it is no longer too hot, the ultrasonic transducer is turned back on in step 456.

In FIG. 5, if the temperature is below the critical temperature $T_{critical}$ at step 450 (or after the ultrasonic transducer is turned back on in step 456), the system determines if the current temperature T is greater than or equal to the threshold temperature $T_{threshold}$ in step 460. If it is greater than or equal to the threshold temperature $T_{threshold}$ at step 460, the system then determines whether the turn counter has a value of 0 in step 510. If the turn counter equals 0 (thus indicating that this is the first time the threshold temperature $T_{threshold}$ has been reached) at step 510, the system presents the operator with the choices of mutable system parameters and/or possible rules concerning system parameters in step 420. If the turn counter does not equal 0 at step 510, the system determines whether the turn counter is greater than x at step 515.

If tile turn counter is lower than x at step 515, the system proceeds by jumping to step 463, where a previously-chosen selected mutable system parameter(s) is changed in the manner chosen by the operator in step 430. If the turn counter equals x (thus indicating that the previous changes to the previously-chosen parameter have been ineffective) at step 515, the system sets the turn counter back to 0 at step 517, and then presents the operator with the choices of mutable system parameters and/or possible rules concerning system parameters in step 420. Then the operator selects the parameter(s) in step 430. After step 430, because the system has already determined that the threshold temperature $T_{threshold}$ has been reached or exceeded (in step 460), the system proceeds in step 463 with changing the selected mutable system parameter in the manner chosen by the operator in step 430.

In FIG. 5, the system adds 1 to the turn counter at step 520 after the change to the mutable system parameter in step 463. After this, the system returns to monitoring the temperature at step 450. A wait step may be added between step 520 and the return to step 450 in order that the selected action have an effect on the temperature before the system begins checking the temperature again.

The two preferred embodiments in FIGS. 4 and 5 may be combined together in other embodiments. For example, the operator could determine rules before the session starts, and then determine particular mutable system parameters once the session has begun. Furthermore, the variations described in one embodiment could also be applied to the other (e.g., the target temperature mentioned in the description of FIG. 4 could just as well be applied to an embodiment of FIG. 5). Additional steps could be added to either embodiment in order to change the mutable system parameter back to its original state after the ultrasonic system has reached a stable lower temperature. Further still, the operator may set a timer for cycling between higher heating and lower heating modes of operation, which will cause the mode to switch, regardless of the current temperature T.

In the various embodiments according to the present invention, the current status of the ultrasonic transducer could be shown on the operator's display. For example, the current temperature T of the patient contacting surface or the current rate of heating (or any current system parameter) could be displayed on the monitor. This information could be displayed in a variety of ways: as gauge icons, as digital readouts, as histograms, or any other manner of indicating a quantity on a screen.

Figure 6:
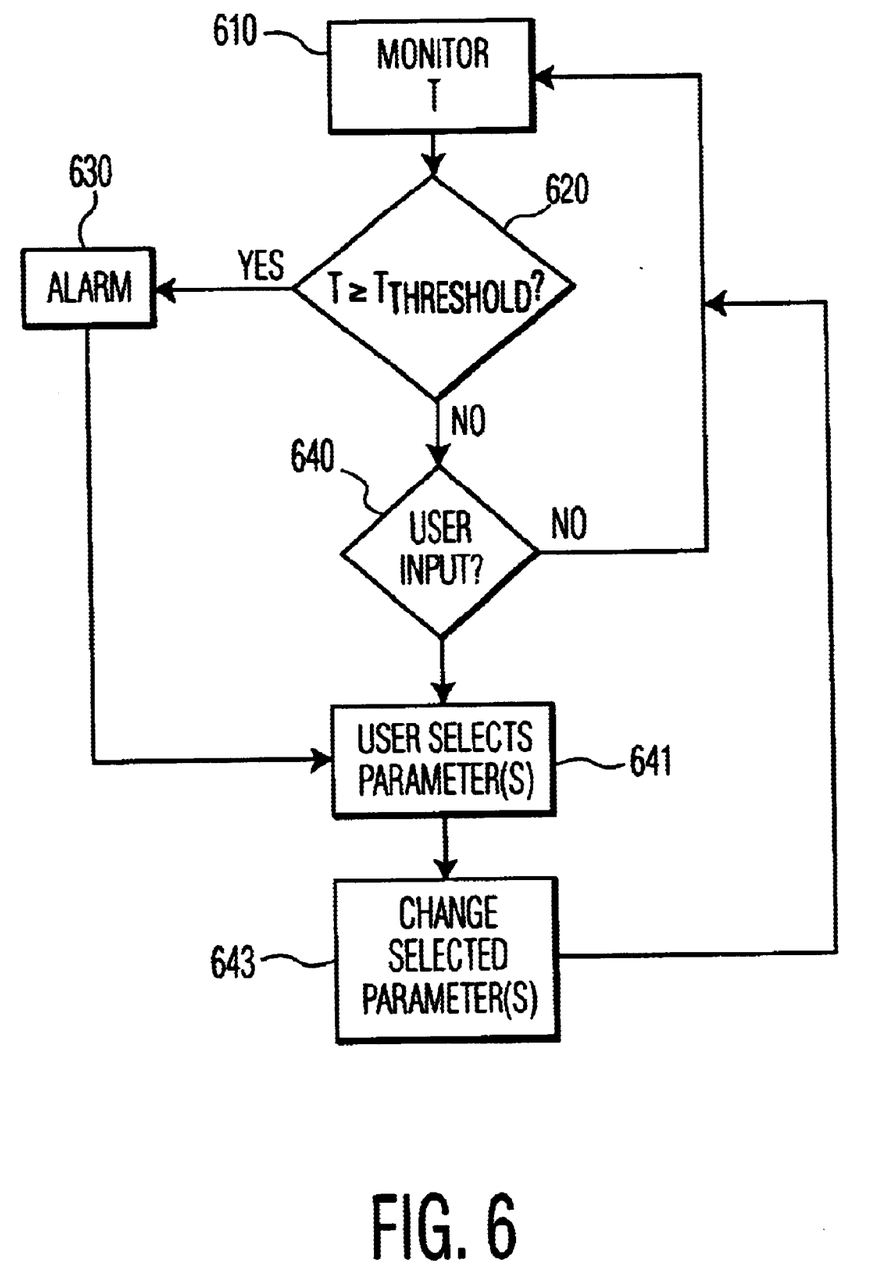
FIG. 6 is a flowchart of yet another preferred embodiment according to the present invention.

In another preferred embodiment, shown in FIG. 6, the user monitors the temperature and other parameters of the ultrasonic system and interacts directly with the system in order to alter the one or more system parameters before the temperature reaches a critical point. Because the user may do this at any point during a session, the system is shown in FIG. 6 as continually checking to see if the user wants to change a parameter. This, as all other steps or procedures in these exemplary preferred embodiments, could be implemented a number of ways. For instance, the system may not be actually "checking" periodically if the user has indicated a desire to alter mutable system parameters. There might be a physical button, or a virtual button shown on the display (and clicked by using the interface), which causes a call, or trap, to the correct sub-program.

In FIG. 6, the system is monitoring the transducer temperature T in step 610. This measured temperature is shown on a display so that the operator may monitor the temperature and act to change mutable system parameters before the temperature is too high. Just in case the operator is distracted, it is also determined if this temperature T has reached a threshold temperature $T_{threshold}$ (when the operator should act before the transducer reaches the critical temperature) at step 620. An alarm is issued in step 630 if the temperature has reached this threshold. This alarm may take any form; for example, it may appear has a bright red flashing blip on the display. If the temperature T is below the threshold temperature $T_{threshold}$ in step 620, the system checks to see if the user wishes to change a mutable system parameter in step 640. As suggested above, a virtual button labeled "Change a parameter?" may be permanently in the corner of the display screen, waiting for the user to click it.

If the user wishes to alter a parameter (or after the alarm has gone off in step 630), the system presents the mutable system parameters to the operator in step 641. Similarly to system checking step 610, this may be implemented in a number of ways. In some embodiments, a display screen (which may be part of the imaging screen) may show the current status of several system parameters in the form of several screen icons and, if the user clicks on the icon, the user will have both indicated his or her desire to change a system parameter and which mutable system parameter he or she wishes to change. The screen icon showing the current status of a mutable system parameter may be displayed in a variety of ways: as gauge icons, as digital readouts, as histograms, or any other manner of indicating a quantity on a screen. The status of practically any mutable system parameter may be viewed (and thus monitored by the operator) in this way. Some examples include the applied voltage, the particular imaging mode of the system, the frame rate, the sector width, etc. In addition, the display may show the time left before the transducer reaches a critical temperature so that the operator may correctly determine the correct time to start altering mutable system parameters.

In a preferred embodiment of the present invention, at least two icons are presented on the screen: probe temperature and power dissipation. Each of these icons depicts these quantities by a bar which changes in size from a <minimum> length (representing a minimum amount) to a <maximum> length (representing a maximum amount), in order that the operator may effectively gauge the effect of, or need for, parameter alteration.

In step 643, the mutable system parameters selected in step 641 are altered by the system in order to reduce the temperature of the ultrasonic transducer. If the user has decided that it is acceptable to change a mutable system parameter in such a way as to create more heat, or if the user had previously changed a parameter in order to decrease the temperature and now wishes to change it back, the mutable system parameters selected in step 641 are also altered by the system in step 643, but this may result in an increase, rather than a decrease, in temperature. After this, the system returns to step 610.

The descriptions above typically refer to the mutable system parameters as being "changed" rather than merely reduced when the threshold temperature $T_{threshold}$ is reached. This is to indicate that the present invention applies to a wide variety of "changes" that may be made to the system parameters in addition to a simple reduction. For example, in another preferred embodiment of the present invention, the mutable system parameter is the imaging mode, and the overheating prevention method consists of switching or "mixing" a high power imaging mode with a lower power imaging mode so that the overall transmit power (and therefore heating) may be reduced. An example of how this may be done is described in the U.S. patent application Ser. No. 10/268,207 entitled "Imaging Ultrasound Transducer System and Method", filed on Oct. 10, 2002 and assigned to the same assignee as the present application. The aforementioned patent application is hereby incorporated by reference.

In such an embodiment (compatible with any of FIGS. 4, 5, or 6), the ultrasonic transducer operates by switching (or cycling) between a higher power imaging mode, such as harmonic imaging, and a lower power imaging mode, such as fundamental (2D) imaging. The various parameters of this switching, e.g. the time period for each mode, the transmit power for each mode, etc., may be selected by the operator or set by the system itself. The operator is given the choice of three different display formats: alternating frames, alternating scan lines, or compound image. In alternating frames mode, the display alternates frames between images based on harmonic imaging and images based on fundamental imaging. This mixed mode produces a flickering appearance, which is not too distracting because the overall effect of the image is as if it was being illuminated by different lighting (not simply alternating bright and dim illumination). This mixed mode can be assisted by automatically adjusting the brightness of the harmonic image to that of the fundamental image.

In alternating scan lines mode, every other line in the scanned plane is scanned with the harmonic image. The resulting combined image is displayed with the regular display averaging which is used to smooth and fill in scan lines. This averaging smoothes the appearance of the image. In compound image mode, a compound image is formed by displaying a central harmonic image of limited width and filling out the edges of the sector with the low power, fundamental mode image.

The preferred embodiments described with reference to FIGS. 4, 5, and 6 above are exemplary and may be altered, combined, and steps in any of them eliminated, as is known to one skilled in the art. The variations described in one embodiment could also be applied to the other (e.g., the target temperature mentioned in the description of FIG. 4 could just as well be applied to an embodiment of FIG. 5). As is discussed above, additional steps could be added to either embodiment in order to change the mutable system parameter back to its original state after the ultrasonic system has reached a stable lower temperature. Further still, the operator or the system may set a timer for how long the system will remain in the changed state, after which the system will reset, regardless of the current temperature.

This system provides the operator with the ability to precisely control the ultrasonic transducer system parameters when cooling down the ultrasonic transducer. Thus, the operator can tailor the system parameter changes to the particular type of imaging being performed.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of cooling an imaging ultrasonic transducer in an imaging ultrasonic transducer system, wherein a patient-contacting surface of said imaging ultrasonic transducer is pressed externally against the skin of a patient in order to generate an image, comprising the steps of:

selecting by an operator at least one mutable system parameter of the imaging ultrasonic transducer system;

determining a temperature of the imaging ultrasonic transducer at the patient-contacting surface; and implementing a parameter change in the selected at least one mutable system parameter based on the determined temperature, wherein the parameter change will cause a reduction, if necessary, in the temperature of the patient-contacting surface of the imaging ultrasonic transducer to prevent damage to the skin of the patient and pain to the patient.

2. The method of claim 1, further comprising the step of:

presenting to the operator at least one mutable system parameter of the imaging ultrasonic transducer system in order for the operator to select at least one mutable system parameter.

3. The method of claim 1, further comprising the steps of:

selecting, by the operator, the parameter change in the selected at least one mutable system parameter.

4. The method of claim 1, wherein the step of implementing the parameter change in at least one mutable system parameter based on the determined temperature comprises the steps of:

determining if the determined temperature is greater than, or equal to, a threshold temperature; and implementing, if it is determined that the determined temperature is greater than, or equal to, a threshold temperature, the parameter change in at least one mutable system parameter.

5. The method of claim 4, wherein said step of selecting by the operator at least one mutable system parameter of the imaging ultrasonic transducer system occurs after it has been determined that the determined temperature is greater than, or equal to, a threshold temperature.

6. The method of claim 4, further comprising the step of:

selecting by the operator the threshold temperature.

7. The method of claim 1, wherein the step of implementing the parameter change in at least one mutable system parameter based on the determined temperature is comprised of the step of:

changing the at least one system parameter, wherein an amount of change in the at least one mutable system parameter is based on an amount of temperature variation from a predetermined operating temperature value.

8. The method of claim 1, wherein said step of selecting by the operator at least one mutable system parameter of the imaging ultrasonic transducer system comprises the step of:

selecting a rule by which the ultrasonic transducer system will implement a rule-based change in the step of implementing the parameter change in the selected at least one mutable system parameter based on the determined temperature.

9. The method of claim 1, wherein a basis of the parameter change is at least one of:

an amount the determined temperature is above or below a predetermined operating temperature value; or whether the determined temperature is equal to or greater than a predetermined threshold temperature value.

10. The method of claim 1, further comprising the step of:

resetting the at least one mutable system parameter back to an original state, said original state being a state of the at least one mutable system parameter before the parameter change was implemented.

11. The method of claim 10, wherein the resetting step is at least one of: a) initiated by an operator of the imaging ultrasonic transducer system, b) initiated by the imaging ultrasonic transducer system when the imaging ultrasonic transducer has cooled sufficiently, and c) initiated by then imaging ultrasonic transducer system after a prescribed period of time.

12. The method as recited in claim 1, further comprising the steps of determining by the imaging ultrasonic transducer system whether the determined temperature of the patient-contacting surface of the imaging ultrasonic transducer is greater than or equal to a critical temperature;

turning the imaging ultrasonic transducer off if it is determined that the determined temperature is greater than or equal to the critical temperature; and once the imaging ultrasonic transducer has been turned off:

determining a current temperature of the patient-contacting surface of the imaging ultrasonic transducer;

determining whether the current temperature is less than the critical temperature; and turning the imaging ultrasonic transducer back on if it is determined that the current temperature is less than the critical temperature.

13. The method as recited in claim 1, wherein the at least one mutable system parameter comprises at least one of:

duty cycle, wherein the duty cycle is a ratio of the time in which the imaging ultrasonic transducer is transmitting to the time in which the imaging ultrasonic transducer is receiving;

applied voltage to transmitting elements in the imaging ultrasonic transducer;

frequency of ultrasonic sound waves transmitted by the imaging ultrasonic transducer;

frame rate of the imaging ultrasonic transducer;

pulse repetition frequency (PRF) of the imaging ultrasonic transducer;

aperture of the imaging ultrasonic transducer;

imaging depth of the imaging ultrasonic transducer;

sector width of the imaging ultrasonic transducer; and imaging mode of the imaging ultrasonic transducer.

14. A system for cooling an imaging ultrasonic transducer in an imaging ultrasonic transducer system, comprising:

a patient-contacting surface of said imaging ultrasonic transducer for pressing externally against the skin of a patient in order to generate an image;

a user interface by which an operator may select at least one mutable system parameter from a displayed at least one mutable system parameter;

at least one temperature sensor for sensing the temperature of the patient-contacting surface of the ultrasonic transducer; and a controller for implementing a parameter change in a selected at least one mutable system parameter based on the sensed temperature, wherein the parameter change will cause a reduction in the temperature of the patient-contacting surface of the imaging ultrasonic transducer to prevent damage to the skin of the patient and pain to the patient.

15. The system of claim 14, further comprising:

means for presenting to the operator at least one mutable system parameter of the imaging ultrasonic transducer system in order for the operator to select at least one mutable system parameter.

16. The system of claim 14 further comprising:

means for selecting, by the operator, the parameter change in the selected at least one mutable system parameter.

17. The system of claim 14, further comprising the step of:

means for resetting the at least one mutable system parameter back to an original state, said original state being a state of the at least one mutable system parameter before the parameter change was implemented.

18. The system of claim 14, wherein the at least one mutable system parameter comprises at least one of:

duty cycle, wherein the duty cycle is a ratio of the time in which the imaging ultrasonic transducer is transmitting to the time in which the imaging ultrasonic transducer is receiving;

applied voltage to transmitting elements in the imaging ultrasonic transducer;

frequency of ultrasonic sound waves transmitted by the imaging ultrasonic transducer;

frame rate of the imaging ultrasonic transducer;

pulse repetition frequency (PRF) of the imaging ultrasonic transducer;

aperture of the imaging ultrasonic transducer;

imaging depth of the imaging ultrasonic transducer;

sector width of the imaging ultrasonic transducer; and imaging mode of the imaging ultrasonic transducer.

\* \* \* \* \*